United States Patent [19]

Edoga

[11] Patent Number: 5,728,047
[45] Date of Patent: Mar. 17, 1998

[54] SURGICAL INSTRUMENT POSITIONING SYSTEM

[75] Inventor: John K. Edoga, Morristown, N.J.

[73] Assignee: SMC Surg-Med Devices, Inc., Morristown, N.J.

[21] Appl. No.: 606,744

[22] Filed: Feb. 27, 1996

Related U.S. Application Data

[63] Continuation-in-part of Ser. No. 519,130, Aug. 24, 1995, abandoned.
[51] Int. Cl.$^6$ .................................................. A61B 11/02
[52] U.S. Cl. ........................ 600/227; 600/229; 600/230; 600/102; 600/204
[58] Field of Search .................... 600/102, 201, 600/204, 207, 227, 229, 230, 231, 233, 234; 604/174, 175, 177, 178, 179, 180; 128/DIG. 26, 96.1, 99.1, 100.1, 105.1, 847, 849, 852; 248/68.1, 74.4, 205.1; 5/503.1, 507, 658

[56] References Cited

U.S. PATENT DOCUMENTS

| | | |
|---|---|---|
| 605,715 | 6/1898 | Hohmann . |
| 2,493,598 | 1/1950 | Rozek ..................................... 600/229 |
| 3,762,401 | 10/1973 | Tupper . |
| 4,380,999 | 4/1983 | Healy . |
| 4,416,664 | 11/1983 | Womack . |
| 4,621,619 | 11/1986 | Sharpe . |
| 5,025,780 | 6/1991 | Farley . |
| 5,183,033 | 2/1993 | Wilk . |
| 5,224,680 | 7/1993 | Greenstein et al. . |
| 5,231,974 | 8/1993 | Giglio et al. . |
| 5,271,745 | 12/1993 | Fentress et al. . |
| 5,334,186 | 8/1994 | Alexander . |
| 5,337,736 | 8/1994 | Reddy . |
| 5,372,147 | 12/1994 | Lathtrop, Jr. et al. . |
| 5,379,758 | 1/1995 | Snyder . |
| 5,415,159 | 5/1995 | Ortiz et al. . |

FOREIGN PATENT DOCUMENTS

| | | | |
|---|---|---|---|
| 2362947 | 6/1975 | Germany | ............................... 600/229 |
| 2223410 | 8/1988 | United Kingdom . | |

*Primary Examiner*—Beverly M. Flanagan
*Attorney, Agent, or Firm*—Lerner, David, Littenberg, Krumholz & Mentlik

[57] ABSTRACT

A surgical instrument positioning system includes a belt assembly positionable adjacent and across the body of the patient and a surgical instrument, such as a retractor, provided with an attachment portion for attachment to one or more of a plurality of adjustment positions provided on the belt assembly.

67 Claims, 3 Drawing Sheets

FIG. 7I

# SURGICAL INSTRUMENT POSITIONING SYSTEM

CROSS-REFERENCE TO RELATED APPLICATION

The present application is a continuation-in-part of U.S. patent application Ser. No. 08/519,130, filed on Aug. 24, 1995, now abandoned, the disclosure of which is incorporated herein by reference.

FIELD OF THE INVENTION

The present invention relates to a surgical instrument positioning system which is particularly useful for maintaining a retractor and other surgical tools in a fixed position during laparoscopic surgery.

BACKGROUND OF THE INVENTION

Many surgical procedures performed today require the use of additional surgeons and/or medical assistants to perform what is considered to be "robotic" tasks during the procedure. For example, laparoscopic cholecystectomy, the removal of the gallbladder, is typically performed by at least two surgeons. An assistant surgeon provides retraction of the right lobe of the liver by grasping the upper portion of the gallbladder using a ratcheted grasper and pushes the liver forward and to the right. Depending on the operating surgeon's preference, the assistant surgeon either also provides additional traction on the gallbladder by grasping the portion of the gallbladder which leads to the bile ducts or he or she holds the laparoscope. This need to use at least two surgeons makes this procedure unnecessarily costly.

Laparoscopic Nissen fundoplication, the repair of hiatal hernias and the creation of a valve to check acid reflux from the stomach into the esophagus, is currently performed by at least three surgeons, increasing costs even more. The first assistant surgeon usually holds the laparoscope and also provides the needed retraction on the stomach and esophagus while the second assistant surgeon retracts the lateral segment of the left lobe of the liver, in most cases, using a fan retractor.

In performance of laparoscopic cholecystectomy, the removal of the gallbladder, the right lobe of the liver is retracted by grasping the gallbladder fundus with a grasper and pushing forward, towards the patient's head, and to the patient's right. Once the required retraction is achieved, a member of the surgical staff, and often a surgeon, must hold and maintain the grasper in the desired position while a second surgeon performs the rest of the procedure.

Besides the increase in costs associated with the need for additional surgeons to mechanically hold surgical instruments in place, problems can also arise during the surgical procedure due to a number of human factors. These problems include the surgeon becoming fatigued or distracted while trying to hold the instrument in a fixed position, or the surgeon unintentionally allowing the instrument to drift from its original position due to a lack of visual reinforcement of the instrument's position within the patient as the surgeon holding the retractor rarely gets a chance to see the retractor position, especially during the critical portions of the procedure. Moreover, the presence of additional surgeons about the patient can interfere with the operative field and the arm movements of the lead surgeon.

There have been a number of attempts to provide positioning systems for holding retractors and other surgical instruments in a fixed position so as to eliminate the need for human involvement. For example, U.S. Pat. No. 4,380,999 to Healy provides a "stepped" surgical retractor including a ladder-like support which is attached via a universal clamp to the operating table and projects vertically upwardly with respect to the operating table. Although this device eliminates the need for a surgeon to hold the retractor in a fixed position, the support structure of the device can interfere with the arms of the surgeon due to its vertical projection into the operative field.

Other retractor or positioning systems, such as U.S. Pat. No. 5,372,147 to Lathrop, Jr. et al., provide mechanical arm devices which are clamped to the side of the operating table and employ a pivoting robotic arm which extends horizontally over the table and patient. These system suffer from the same problem as with the device of Healy in that they are located in the operative area above the patient and can interfere with the movements of the surgeon. These devices can also be cumbersome and difficult to use. Furthermore, such systems are relatively expensive, especially when provided with hydraulic or motor-assisted lifting mechanisms.

Accordingly, there is a great and longfelt need to provide a positioning system for use during surgical procedures, such as during laparoscopic surgery, which is relatively simple to use, inexpensive, and which solves the aforementioned problems associated with the use of assistant surgeons and positioning systems which can interfere with the surgeon.

SUMMARY OF THE INVENTION

The aforementioned shortcomings of prior instrument positioning systems have been addressed by the present invention, which in one preferred embodiment provides a positioning system for use during surgical procedures including a belt assembly positionable adjacent and across a bodily surface of a patient and having positioning means for providing a plurality of adjustment positions. A surgical instrument is provided comprising an attachment portion and/or attachment means for adjustable attachment to the adjustment positions provided by the positioning means of the belt assembly to allow the instrument to be maintained in a desired position during a surgical procedure. The belt assembly for use in such a surgical instrument positioning system can be separately provided.

The positioning means can include, for example, a plurality of raised ridge members defining a plurality of slots therebetween to removably retain said attachment portion of said surgical instrument. The positioning means can further include a plurality of loop members defining a plurality of orifices therebetween, the loop members and orifices being adapted to removably retain the attachment portion of said surgical instrument.

Still further, the positioning means may include a plurality of strings adapted to removably retain the attachment portion of the surgical instrument to said belt assembly. In this ease, the surgical instrument can be formed with one or more annual slots for receiving portions of the strings used to retain the surgical instrument. Alternatively, the positioning means can comprise a plurality of instrument slots formed in the belt assembly to removably retain a scissors-like handle portion of the surgical instrument or can comprise one or more post members positioned in the belt assembly to removably retain the scissors-like handle portion of the instrument disposed about the post member.

In another arrangement, the positioning means can comprise abutment means for providing an abutment surface transverse to the bodily surface of the patient for retaining the attachment portion of the surgical instrument in a fixed position. Here, the belt assembly can include a central portion and the abutment means can be in the form of an abutment wall disposed on the central portion of the belt assembly. The abutment wall can include a plurality of raised ridges defining a plurality of abutment surfaces therebetween for retaining the attachment portion of the surgical instrument in a fixed position. Alternatively, the abutment wall can be provided with a plurality of sockets for retaining the attachment portion of said surgical instrument in a fixed position. The abutment wall can also be constructed so as to be displaceable along said central portion of said belt assembly.

Still further, the positioning means can comprises hook and loop fastener provided on both the belt assembly and on the attachment portion of the surgical instrument to removably retain the surgical instrument.

Preferably, the belt assembly further includes securement means for securing the belt assembly across the patient and to an operating table beneath the patient. The securement means desirably includes a pair of adjustable straps attached to opposite sides of the belt assembly and fastening hooks attached to the straps for removable engagement with the operating table.

The belt assembly preferably comprises a central portion having an elongate opening therein, and the positioning means preferably consists of a plurality of post members forming a ladder-like arrangement disposed across the opening. The attachment means of the surgical instrument preferably comprises a removably attachable instrument hook for removable attachment to at least one of the post members. The post members each preferably have a exposed length of about 100–150 mm and is about 0.5 to 1.0 mm greater than the length of the instrument hook.

The instrument hook can be provided on a self-locking ring member having a diameter approximately corresponding to a diameter of a portion of the surgical instrument, or can be integrally formed with the surgical instrument. The surgical instrument may comprise a retractor, such as a laparoscopic fan retractor, a ratcheted grasper, or any similar type of instrument.

The elongate body of the central portion of the belt can be formed from a flexible plastic material capable of substantially conforming to the contour of the bodily surface of the patient, and can be shaped in a curved or arch-like configuration when the central portion is in a flat condition. In a preferred embodiment of the present invention, the central portion of the belt assembly is provided with a hollow area to allow inflation thereof.

In a further preferred embodiment, the belt assembly can further be provided with auxiliary fastening means for removably retaining miscellaneous objects, such as holsters for suction and cautery devices.

The present invention also provides a method of positioning a surgical instrument during a surgical procedure comprising the steps of (a) securing a belt assembly adjacent and across a bodily surface of a patient, the belt assembly comprising positioning means for providing a plurality of adjustment positions; (b) positioning the surgical instrument in a desired position, the surgical instrument including an attachment portion and/or attachment means for adjustable attachment to the adjustment positions provided by the positioning means of the belt assembly; and (c) attaching the attachment portion of the surgical instrument to the positioning means of the belt assembly so that the surgical instrument is maintained in a desired position during the surgical procedure.

The method may further comprise the step of securing the belt assembly to an operating table beneath the patient. Where the surgical instrument comprises a retractor, the method preferably includes the steps of inserting the retractor into the body of the patient through an opening therein, moving the retractor into a first position, and pivoting the retractor about the opening to move the retractor to the desired position.

Where the belt assembly includes a plurality of post members forming a ladder-like arrangement and the attachment means includes an instrument hook, the step of attaching preferably includes locking the instrument hook around at least one of the post members. Where the belt assembly includes a central portion having a hollow area therein to allow inflation of the central portion, the method can further include the step of inflating the central portion so that the belt assembly fits securely across the bodily surface of the patient. Finally, where the attachment means comprises removably attachable instrument hook, the method may further include the step of attaching the instrument hook to the surgical instrument.

The present invention in another aspect further provides a method of retracting an organ during a laparoscopic surgical procedure comprising the steps of (a) securing a belt assembly adjacent and across the abdomen of a patient and to an operating table beneath the patient, the belt assembly having positioning means for providing a plurality of adjustment positions; (b) inserting a retractor into the body of the patient through an opening therein, the fan retractor comprising attachment means for attachment to the adjustment positions provided by the positioning means of the belt assembly; (c) moving the retractor into a first position; (d) pivoting the fan retractor about the opening to move the retractor so as to retract the organ to a desired position; and (f) attaching the attachment means of the retractor to the positioning means of the belt assembly so that the retractor is maintained in a desired position during the surgical procedure.

In yet another aspect, the present invention further provides a method of positioning a retractor during a surgical procedure comprising the steps of (a) securing a belt assembly adjacent and across a bodily surface of a patient, the belt assembly comprising positioning means for providing a plurality of adjustment positions, the positioning means comprising a plurality of post members forming a ladder-like arrangement; (b) providing a retractor having a hook for engagement with the post members of the belt assembly; and (c) hooking the hook of the retractor to at least one of the post members to position the retractor in a desired position for the surgical procedure.

DETAILED DESCRIPTION OF PREFERRED EMBODIMENTS

Figure 1:
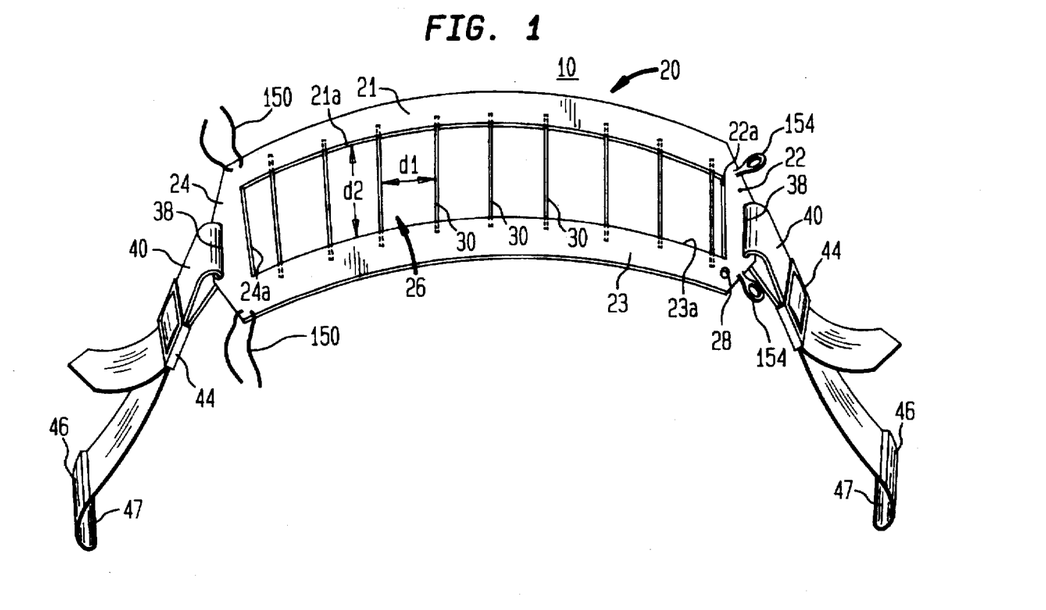
FIG. 1 is a front perspective view of a belt assembly in accordance with a preferred embodiment of the present invention.

Referring to FIG. 1, a belt assembly used in accordance with a preferred embodiment of the present invention is generally designated as 10. In this preferred embodiment, belt assembly 10 includes a central member 20 which includes an upper portion 21, lower portion 23 and side portions 22 and 24, which border an elongate opening 26. Elongate opening 26 is surrounded by inner walls 21a, 22a, 23a and 24a of upper, lower and side portions 21, 22, 23 and 24, respectively. Central member 20 can be formed from a single piece of molded plastic or, alternatively, can be formed with a hollow bladder that can be inflated with a gas, such as carbon dioxide, through an opening which shown in phantom as 28.

Positioned across elongate opening 26 is a plurality of post members 30, which are arranged parallel to one another and extend from inner wall 21a to inner wall 23a. Post members 30 have an exposed length within opening 26 equal to the width $d_2$ of elongate opening 26. Post members 30 are formed to be slightly longer than width $d_2$, which is preferably between 100 to 150 mm so they extend into central portion 20. Post members 30 are preferably made from a metal and are separated from one another by a distance $d_1$ of about 20 to 30 mm.

When formed as a solid piece, central portion 24 is preferably molded from a flexible material such as a semi-rigid plastic so that it is durable but has sufficient flexibility to conform to the surface of the patient to which it is applied. For instance, when belt assembly 10 is strapped over the abdomen of a patient during laparoscopic surgery, central portion 24 should generally conform to the contour of the patient's abdomen. The belt assembly 10 can also be formed so as to be positioned across other bodily portions such as the chest, arm or leg. Alternatively, when formed to be inflatable, central portion 10 is preferably made from a pair of thin flexible plastic sheets attached about their edges to form a bladder which is inflatable to further increase the snugness of the belt assembly to the patient. In such case, once the belt assembly 10 is positioned across the patient and hooked to the operating table, it can then be inflated with a gas such as carbon dioxide or other available gas in the operating room. The entire belt's central member 20 may be inflatable, or, in the alternative, the central member may be constructed with a number of smaller, discrete inflatable bladders or pockets which may be selectively filled. Thus, for example, the ends of the central member 20 may be inflated to ensure that the central member remains relatively planar on top yet conforms better to the curvature of the torso and can even provided additional space between the central member and the torso for more easily attaching the surgical instrument to the belt assembly as described below. The entire belt assembly can be inexpensively manufactured so as to be disposable after it is used in surgery. The belt assembly can be hooked to the operating table, hook to itself under the operating table or can be secured about the patient's mid-section, arm, leg, etc. such that it remains stable and secure during the operating procedure.

Side portions 22 and 24 include openings 38 for attachment of securement straps 40. Securement straps 40 include adjustment buckles 44 to allow the length of the straps to be adjusted to the desired length according to the girth of the patient and particular desired attachment location. Other adjustment means besides buckles can obviously be used such as providing stretchable or elastic securement straps, using multiple strap portions attachable together by Velcro fastener or snap fittings, etc. Attached to the ends of securement straps 40 are hooks 46 which include curved portions 47 for attachment to a rail member 106 or other portion of an operating table (see FIG. 6). Hooks 46 need not be provided and other ways of attaching the belt assembly 10 to the operating table (or other stable fixture in the operating room) can be used instead, such as providing holes in the ends of the securement straps 40 which fit over posts provided on the operating table. Buckles and/or snap fittings may also be used.

Figure 2:
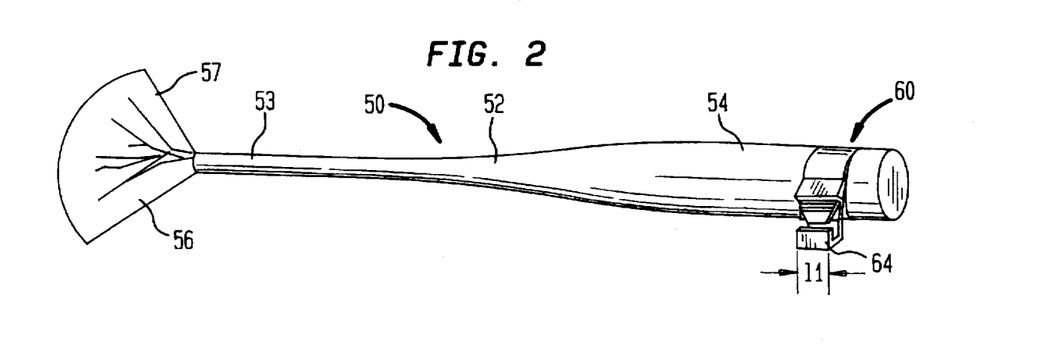
FIG. 2 is a perspective view of a retractor and instrument hook in accordance with one embodiment of the present invention.
Figure 3A:
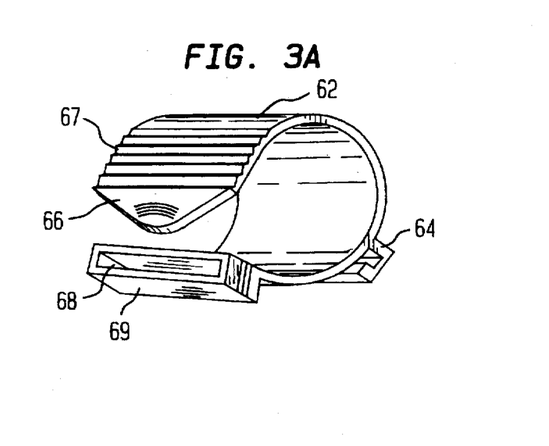
FIG. 3A is a front perspective view of the instrument hook shown in FIG. 2.
Figure 3B:
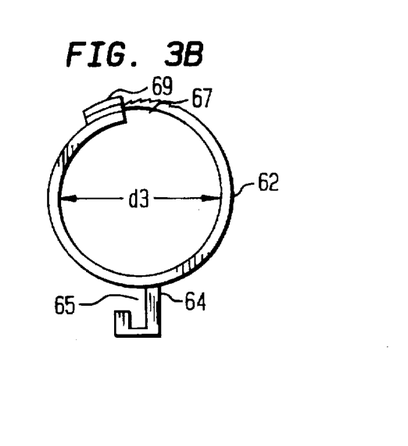
FIG. 3B is a side view of the instrument hook shown in FIG. 3A.
Figure 4:
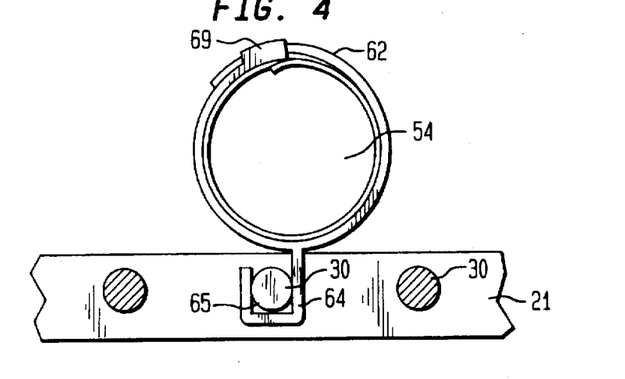
FIG. 4 is an enlarged, diagrammatic, side view of the instrument hook engaged with the belt assembly.

Referring to FIG. 2, a surgical instrument 50 is shown, which in this case is depicted as a laparoscopic fan retractor. Surgical instrument 50 includes a handle 52 and an expandable fan blade 56 with spreadable digits 57. The retractor is used to retract bodily organs such as the liver during laparoscopic surgery. Handle 52 of instrument 50 includes a distal end 53, at which fan blade 56 is attached, and a proximal end 54, to which an instrument hook 60 is attached. As shown in FIGS. 3A and 3B, instrument hook 60 is preferably removably attachable to the distal end 53 of the surgical instrument. Instrument hook 60 includes a J-shaped hook member 64 integrally formed therewith. Hook member 64 defines a groove 65 therein which is formed to hook around a post member 30 of belt assembly 10, as shown in detail in FIG. 4. Preferably, the length $l_1$ of hook member 64 is about equal to length of the exposed portion of the post members 30 or the width d2 of elongate opening 26. More preferably, the length $l_1$ is about 0.5 to 1 mm less than the width $d_2$ so as to allow easy placement of the hook member 64 around a post 30 and to ensure a good frictional fit between inner walls 21a and 23a. It should also be appreciated that the length of the hook member $l_1$ need not closely match the width d2 of elongate opening 26, and shorter lengths of hook member $l_1$ can be provided. In addition, it is possible that hook member 64 have a smaller length than the width of the instrument hook 60.

Instrument hook 60, in a preferred embodiment, is attachable to surgical instrument 50 and includes a self-locking ring member 62 and a tongue member 66 which fits within a slot 68 which is formed within end portion 69 of ring member 62. Tongue member 66 includes a plurality of raised ridge 67 for frictional engagement within slot 68 to enable adjustment of the diameter of ring member 62 to fit the diameter of the surgical instrument to which it is attached. Instrument hook 60 is preferably provided in two sizes, one with an inner diameter $d_3$ of 3 to 5 mm and the other with an inner diameter of 10–12 mm, which allows the hook 60 to fit around typically used surgical instruments having distal handle diameters of corresponding sizes.

Although instrument hook 60 is preferably provided as a separate member which is removably attachable to a given surgical instrument, it is also possible that it can be permanently attached to the instrument or formed integral there with. In addition, when instrument hook 60 is separately provided, it can be attached to the surgical instrument in a number of ways besides a tongue and slot arrangement. For example, Velcro fasteners can be used to secure the ring member to the instrument or to itself once placed around the instrument. Other possible attachment arrangements include snap fasteners, gluing the hook to the instrument, or providing a narrowing diameter of the ring member 62 such that it can be slipped onto the handle and frictionally lock once pushed a given distance. Although only a single hook member 64 is shown in the figures, two or more such hook members can be provided so as to hook onto two or more post members 30 of belt assembly 30 and to provide increased stabilization to the surgical instrument.

Besides being provided with a plurality of post members, belt assembly 10 can also support one or more auxiliary fastening devices, such as straps 150 and suspenders 154 (FIG. 1). Such fastening devices can be used for holding and securing other items that tend to lie across the body of the patient during surgery, and can comprise small clips, Velcro straps, straps with snaps or other type of similar fastening elements. For instance, straps 150 could be used for holding laparoscope light cords or gas hoses such as $CO_2$ lines. Suspenders 154 could be used for holding in place holsters for suction and cautery devices. The fastening elements are preferably placed near the openings 38 but can also be located along any portion of central member 20. With these additional fastening devices, belt assembly 10 can therefore also function as an OR utility belt to assist the surgeon in holding other items in a secure position, away from the operating area of the patient.

Figure 5:
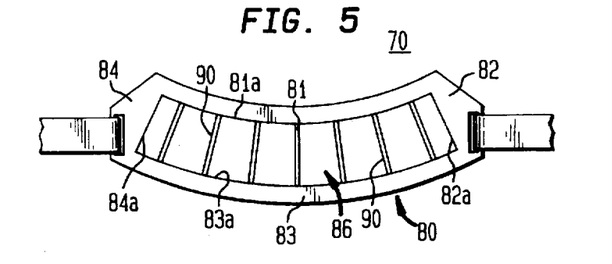
FIG. 5 is a top elevation view of a belt assembly of the present invention in accordance with another preferred embodiment.

FIG. 5 shows an alternate embodiment of belt assembly, generally designated as 70, including a central member 80. Central member 80 includes an upper portion 81, lower portion 83 and side portions 82 and 84, forming a border around elongate opening 86. Elongate opening 86 is surrounded by inner walls 81a, 82a, 83a and 84a of upper, lower and side portions 81, 82, 83 and 84, respectively. In this embodiment, however, inner walls 81a and 83a, in addition to being parallel with one another, lie along curved line segments when belt assembly 70 is in a flat condition. This arrangement results in a central portion which is curved with the post members tapering slightly inward toward a common point at a distance from central member 80. The tapered positioned of the post members 90 allows for a better fit around the natural configuration of the human torso, especially in massively obese or pear-shaped patients. Central member 80 of this embodiment can also be provided with an inflatable hollow bladder to increase snugness in fit.

Figure 6:
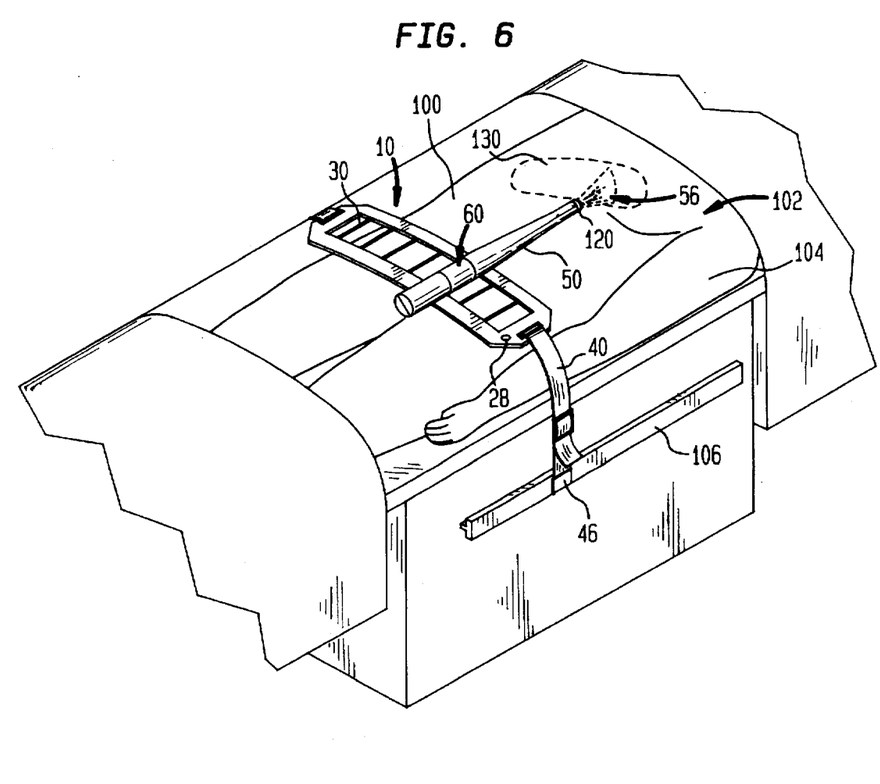
FIG. 6 is an elevational, partial view of the positioning system used during laparoscopic surgery.

Referring now to FIG. 6, the positioning system, including the belt assembly 10 and instrument hook 60 attached to surgical instrument 50, is shown in use during a surgical procedure which requires laparoscopic retraction of an internal organ in a sideways or lateral direction relative to the elongation direction of the patient from head to toe. In accordance with a preferred method of positioning a surgical instrument during a surgical procedure, the following steps are employed. First, the belt assembly 10 is positioned over and across the abdomen 100 of the patient 102 lying on an operating table 104. The hooks 46 of belt assembly 10 are the hooked to rails 106, which are typically attached on both sides of the operating table. The straps 40 can then be adjusted to ensure that the belt assembly fits securely and snugly about the abdomen of the patient. If the belt assembly is inflatable, it can then be inflated through opening 28 to enhance the fit to the patient.

Next, the surgical instrument 50, here a fan retractor with the instrument clip 60, is provided to the surgeon. The clip 60, if provided separately, can be attached to the retractor in advance of the surgery or can quickly be placed on the instrument moments before the retractor is needed.

The retractor is then inserted with the fan blade 56 in a folded position into the patient through a trocar port 120, which is the tube through which the instrument is inserted into the patient. Once inserted, the fan blade is opened by moving apart spreadable digits 57. The retractor is then moved to a desired position to retract the internal organ 130, such as a lobe of the liver, and locked into a fixed position by attaching the instrument clip 60 to the most appropriate post members 30 on the belt assembly. Typically, the trocar port 120 provides a pivot point about which the surgical instrument can be pivoted to laterally retract the organ.

Numerous advantages are provided by the positioning system according to the present invention. Most importantly, the present invention eliminates the need for additional surgeons or assistants to robotically hold surgical instruments, such as retractors, during lengthy surgical procedures.

However, many other advantages are achieved by the present invention. For instance, the system is self-contained. Thus, it requires no outside lines such as suction tubes to be operational. No complicated assembly of the system is required, and the system can be inexpensively manufactured, since it preferably comprises two parts, the belt assembly and the self-locking instrument clip.

Importantly, the present system is low profile, i.e., it will not intrude into the operative field and therefore will not interfere with the arms of the surgeon as is the case with other types of surgical instrument positioning systems.

The present system is also adjustable to accommodate a wide range in patient girths, and is adjustable to fit different sized surgical instruments, such as commonly used laparoscopic retractors and graspers. The system can also be fully disposable eliminating the need for re-sterilization.

The present system is especially adapted for use in laparoscopic repair of the hiatal and paraesophageal hernias where a fan retractor is used to retract the lateral segment of the left lobe of the liver. In this procedure, leveraged retraction is achieved by pushing the shaft of the fan retractor against the patient's body with the fan shaped end appropriately positioned under the lateral segment of the left lobe of the liver. Once the liver has been retracted to the appropriate position, the instrument hook is fastened to the nearest post member 30 so as to maintain the retraction during the surgical procedure.

The present invention can also be used in the performance of laparoscopic cholecystectomy, the removal of the gallbladder, where the right lobe of the liver is retracted by grasping the gallbladder fundus with a 5 mm grasper and pushing forward and to the patient's right. Once the required retraction is achieved, the end portion of the grasper can be positioned to abut inner wall 21a and/or can be clipped onto the belt as described above to provide forward retraction in the direction towards the head of the patient. The surgeon himself provides the retraction of the gallbladder ampulla with his left hand and the performs the dissection with the his right hand.

Figure 7A:
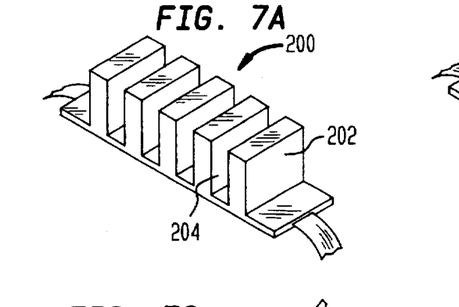
FIGS. 7A to 7I illustrate a number of possible embodiments for attaching the surgical instrument to the belt assembly in accordance with the present invention.
Figure 7B:
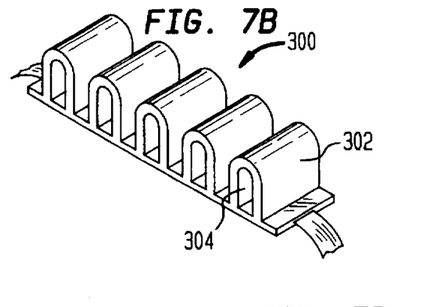
Figure 7C:
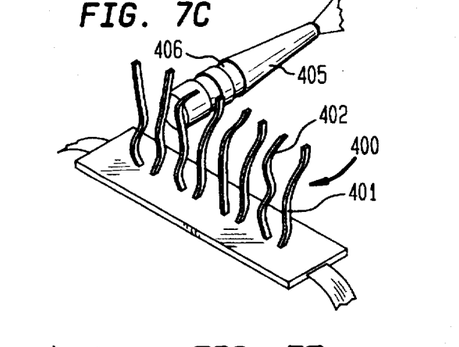
Figure 7D:
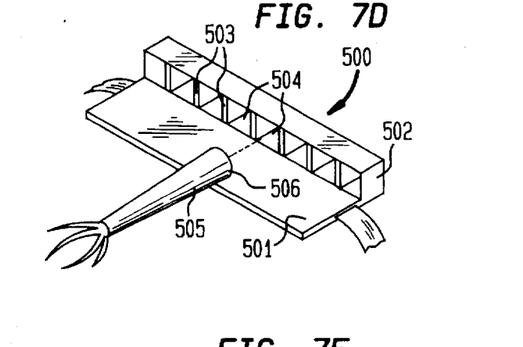
Figure 7E:
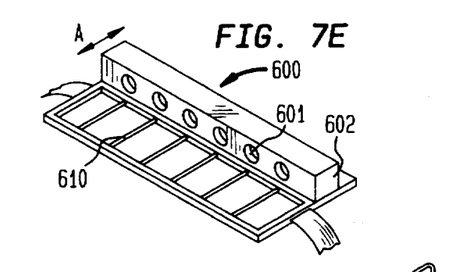

Referring now to FIGS. 7A through 7F, there is shown a number of possible embodiments of the belt assembly and surgical instrument that can be used in accordance with the present invention. It should be appreciated that these embodiments can be used by themselves or in combination with each other on a single belt. Belts can also combine the these structures with the structure shown in FIG. 1 as illustrated in FIG. 7E. Furthermore, the belt of this invention can be constructed such that the following securing and positioning schemes and devices can be interchangeable.

As shown in FIG. 7A, one embodiment of belt assembly 200 contains a number of raised ridge members 202 which form a plurality of slots 204 therebetween. In this embodiment, the surgical instrument to be used (such as a retractor) can be slipped into the closest slot 204 once the proper retraction is attained by the surgeon. In this scenario, the end of the surgical instrument insertable into the slots 204 constitutes the attachment portion of the instrument. The attachment portion of the instrument, therefore, need not necessarily include any type of clip or hook and may simply comprise the distal end portion of the instrument. The material forming belt assembly 200 can comprise foam rubber or other high frictional material such that the end of the surgical instrument is held in place and will not slip once inserted into a desired slot 204. These slots can be provided at an angle to better accommodate the angled position of the retractor when in position. Alternatively, a rear wall can be added behind the slots 204 to prevent lateral movement of the end of the surgical instrument.

Similarly, as shown in FIG. 7B, the belt assembly 300 can include a plurality of loop members creating a plurality of corresponding orifices 304 into which the end of the surgical instrument can be inserted for holding the instrument in place during the surgical procedure. These loops can also be closed along the back edge such that they can receive and urge forward a grasper.

Referring now to FIG. 7C, another possible embodiment of the belt assembly 400 is shown, in which a plurality of fastening strings 401, 402 are provided to tie over the end of the surgical instrument 405. The surgical instrument can also include one or more annular slots 406 which the strings can fit into to help hold the instrument in place. Alternatively, the fastening strings can be replaced with fastening straps which can include straps attachable by Velcro fastener, buckles, snaps, etc.

A further possible embodiment is shown in FIG. 7D in which the belt assembly 500 includes a lower portion 501 intended to fit over the abdomen of the patient and a rear wall 502 which projects upward from the lower portion 501. Rear wall 502 includes a plurality of raised ridges 503 creating a number of abutment surfaces 504 therebetween. This embodiment is especially useful when the surgeon is performing a surgical procedure in which a ratched grasper 505 is used to provide forward traction to an internal organ. With this embodiment, once the surgeon provides the desired forward traction to the internal organ, the end 506 of the grasper 505 is placed into abutment with the nearest desired abutment surface 504. The raised ridges 503 prevent side to side movement of the grasper.

The belt member of the present invention can comprise a combination if the attachment features as described above. For instance, referring now to FIG. 7E, belt member 600 may include both a rear wall 602 for use with providing forward traction, and a plurality of post members 610 for providing attachment positions for an instrument with a clip. In this embodiment, however, rear wall 602 is provided with a number of instrument sockets 601 which are constructed to receive the end of the surgical instrument. Furthermore, rear wall 602 can be lockingly adjustable in the forward and backward direction (along the direction of arrow A) such that in the event that the end instrument is pushed to a position more forward than the initial position of the rear wall, the rear wall can be moved forward to accommodate the desired forward position of the instrument.

Figure 7F:
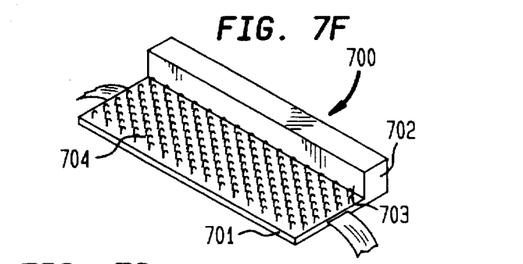

In the embodiment shown in FIG. 7F, the belt assembly 700 can include lower portion 701 and a rear wall 702 where the outer surfaces 703 and 704 can be covered with hook or loop fastener such as Velcro fastener. In this case, the end portion of the surgical instrument can likewise be provided with corresponding loops or hooks so that the instrument can be removably attached to the belt assembly in any desired position.

Figure 7G:
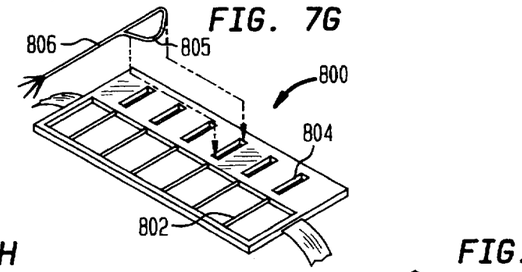

In the embodiment of FIG. 7G, the belt assembly 800 can include a plurality of post members 802 for providing attachment positions for an instrument with a clip. In this embodiment, however, the belt assembly is also provided with a number of instrument slots 804 which are constructed to frictionally receive and retain the scissors-like handle 805 of a typical 5 mm laparoscopic grasper 806.

Figure 7H:
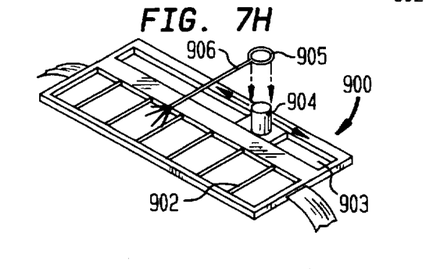
Figure 7I:
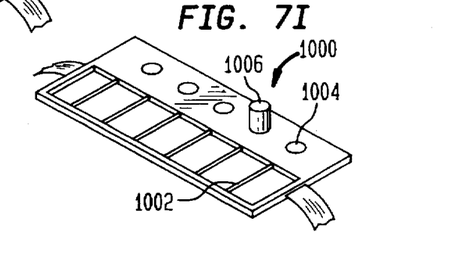

In the embodiment of FIG. 7H, the belt assembly 900 can include a plurality of post members 902 for providing attachment positions for an instrument with a clip. In this embodiment, however, the belt assembly can also be provided with one or more post members 904, positionally adjustable within slot 903, to frictionally receive and retain the scissors-like handle 905 of a typical 5 mm laparoscopic grasper 904 disposed around the post member. Alternatively, in the embodiment of FIG. 7I, a plurality of post-receiving holes 1004 can be formed within belt assembly 1000 in addition to post members 1002. A plurality of posts 1006 can be provided for each respective hole 1004 or a single, removable post 1006 can be used for replacement into the appropriate hole once the desired retraction position is reached, such that the scissors-like handle of a grasper can be retained around the post member.

It should be readily apparent to those skilled in the art that almost any type of attachment method or device can be used to attach the surgical instrument to the belt assembly in accordance with the present invention. For instance, other such attachment means could include pegs projecting from the belt which can fit into one or more holes in the surgical instrument, interlocking belt members which can be closed upon one another with the surgical instrument sandwiched therebetween at the proper position, small clips provided on the belt assembly for clipping into place the surgical instrument, etc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangement may be devised without departing from the spirit and scope of the present invention as set forth in the appended claims.

What is claimed is:

1. A positioning system for use during laparoscopic surgical procedures in which a laparoscopic opening is formed in a patient comprising:

(a) a belt assembly positionable adjacent and across a bodily surface of a patient, said belt assembly comprising positioning means for providing a plurality of adjustment positions, and (b) a laparoscopic surgical instrument having a distal end insertable into said opening to engage an internal organ and comprising attachment means for adjustable attachment to said adjustment positions provided by said positioning means of said belt assembly to allow said distal end of said instrument to be inserted into said opening and maintained in a desired position engaging an internal organ during a laparoscopic surgical procedure.

2. A positioning system as claimed in claim 1, wherein said positioning means comprises a plurality of raised ridge members defining a plurality of slots therebetween, said slots being adapted to removably retain said attachment portion of said surgical instrument.

3. A positioning system as claimed in claim 1, wherein said positioning means comprises a plurality of loop members defining a plurality of orifices therebetween, said loop members and orifices being adapted to removably retain said attachment portion of said surgical instrument.

4. A positioning system as claimed in claim 1, wherein said positioning means comprises a plurality of strings being adapted to removably retain said attachment portion of said surgical instrument to said belt assembly.

5. A positioning system as claimed in claim 4, wherein said surgical instrument comprises one or more annual slots for receiving at least portions of said strings used to retain said surgical instrument, said annual slots being disposed at the location of said attachment portion of said surgical instrument.

6. A positioning system as claimed in claim 1, wherein said positioning means comprises abutment means for providing an abutment surface transverse to the bodily surface of the patient for retaining said attachment portion of said surgical instrument in a fixed position.

7. A positioning system as claimed in claim 6, wherein said belt assembly comprises a central portion and said abutment means comprises an abutment wall disposed on said central portion of said belt assembly.

8. A positioning system as claimed in claim 7, wherein said abutment wall is provided with a plurality of raised ridges defining a plurality of abutment surfaces therebetween for retaining said attachment portion of said surgical instrument in a fixed position.

9. A positioning system as claimed in claim 7, wherein said abutment wall is provided with a plurality of sockets for retaining said attachment portion of said surgical instrument in a fixed position.

10. A positioning system as claimed in claim 7, wherein said abutment wall is displaceable along said central portion of said belt assembly.

11. A positioning system as claimed in claim 1, wherein said positioning means comprises hook and loop fastener provided on both said belt assembly and on said attachment portion of said surgical instrument to removably retain said surgical instrument.

12. A positioning system as claimed in claim 1, wherein said positioning means comprises a plurality of instrument slots formed in said belt assembly to removably retain a scissors-like handle portion of said surgical instrument.

13. A positioning system as claimed in claim 1, wherein said positioning means comprises one or more post members positioned in said belt assembly to removably retain a scissors-like handle portion of said surgical instrument disposed around said post member.

14. A positioning system as claimed in claim 1, wherein said positioning means is removably attachable to said belt assembly.

15. A positioning system as claimed in claim 1, wherein said positioning means are selected from a set of two or more different positioning means which are interchangeable with one another on said belt assembly.

16. A positioning system as claimed in claim 1, wherein said belt assembly further comprises securement means for securing said belt assembly across the patient and to an operating table beneath the patient.

17. A positioning system as claimed in claim 16, wherein said belt assembly comprises a central portion having an elongate opening therein, said positioning means comprises a plurality of post members disposed across said opening, and said attachment means comprises an instrument hook for removable attachment to at least one of said post members.

18. A positioning system as claimed in claim 17, wherein said post members form a ladder-like arrangement.

19. A positioning system as claimed in claim 17, wherein said central portion is provided with a hollow area to allow inflation of said central portion.

20. A positioning system as claimed in claim 17, wherein said instrument hook is removably attachable from said surgical instrument.

21. A positioning system as claimed in claim 20, wherein said instrument hook is provided on a ting member having a diameter approximately corresponding to a diameter of a portion of said surgical instrument.

22. A positioning system as claimed in claim 21, wherein said ring member comprises self-locking attachment means for removable attachment to said surgical instrument.

23. A positioning system as claimed in claim 17, wherein said instrument hook is integrally formed with said surgical instrument.

24. A positioning system as claimed in claim 17, wherein said elongate opening is surrounded by opposed upper and lower edges and by a pair of opposed side edges, said upper and lower edges extending substantially concentric to one another along concentric curved line segments when said central portion is in a flat condition.

25. A positioning system as claimed in claim 17, wherein said elongate body is formed from a flexible material capable of substantially conforming to the contour of the bodily surface of the patient.

26. A positioning system as claimed in claim 1, wherein said surgical instrument comprises a retractor.

27. A positioning system as claimed in claim 1, wherein said belt assembly is constructed and arranged to be positioned across the abdomen of the patient.

28. A positioning system as claimed in claim 1, wherein said belt assembly further comprises auxiliary fastening means for removably retaining cord-like objects during surgery.

29. A positioning system as claimed in claim 1, further comprising a trocar port located at the laparoscopic opening whereby said distal end of said surgical instrument is insertable into the patient through said trocar port.

30. A positioning system as claimed in claim 29, wherein said belt assembly comprises a central portion having an elongate opening therein, said positioning means comprises a plurality of post members disposed across said opening, and said attachment means comprises an instrument hook for removable attachment to at least one of said post members.

31. A positioning system as claimed in claim 30, wherein said post members form a ladder-like arrangement.

32. A positioning system as claimed in claim 30, wherein said instrument hook is removably attachable from said surgical instrument.

33. A positioning system as claimed in claim 30, wherein said instrument hook is integrally formed with said surgical instrument.

34. A belt assembly for use in a laparoscopic surgical instrument positioning system used during laparoscopic surgical procedures in which a laparoscopic opening is formed in a patient, said belt assembly comprising:

(a) an elongate body portion positionable adjacent and across a bodily surface of a patient, and (b) positioning means for providing a plurality of adjustment positions for attachment of an attachment portion of a laparoscopic surgical instrument having a distal end adapted engaging an internal organ to allow said distal end of said instrument inserted into said opening and to be maintained in a desired position engaging an internal organ during a laparoscopic surgical procedure.

35. A belt assembly as claimed in claim 34, wherein said positioning means comprises a plurality of raised ridge members defining a plurality of slots therebetween, said slots being adapted to removably retain the attachment portion of said surgical instrument.

36. A belt assembly as claimed in claim 34, wherein said positioning means comprises a plurality of loop members defining a plurality of orifices therebetween, said loop members and orifices being adapted to removably retain the attachment portion of the surgical instrument.

37. A belt assembly as claimed in claim 34, wherein said positioning means comprises a plurality of strings being adapted to removably retain the attachment portion of the surgical instrument to said belt assembly.

38. A belt assembly as claimed in claim 34, wherein said positioning means comprises abutment means for providing an abutment surface transverse to the surface of the patient for retaining the attachment portion of the surgical instrument in a fixed position.

39. A belt assembly as claimed in claim 38, wherein said belt assembly comprises a central portion and said abutment means comprises an abutment wall disposed on said central portion of said belt assembly.

40. A belt assembly as claimed in claim 39, wherein said abutment wall is provided with a plurality of raised ridges defining a plurality of abutment surfaces therebetween for retaining the attachment portion of the surgical instrument in a fixed position.

41. A belt assembly as claimed in claim 39, wherein said abutment wall is provided with a plurality of sockets for retaining the attachment portion of the surgical instrument in a fixed position.

42. A belt assembly as claimed in claim 39, wherein said abutment wall is displaceable along said central portion of said belt assembly.

43. A belt assembly as claimed in claim 34, wherein said positioning means comprises hook and loop fastener provided on both said belt assembly and on the attachment portion of the surgical instrument to removably retain the surgical instrument.

44. A belt assembly as claimed in claim 34, wherein said positioning means comprises a plurality of instrument slots formed in said belt assembly to removably retain a scissors-like handle portion of said surgical instrument.

45. A belt assembly as claimed in claim 34, wherein said positioning means comprises one or more post members positioned in said belt assembly to removably retain a scissors-like handle portion of said surgical instrument disposed around said post member.

46. A belt assembly as claimed in claim 34, wherein said positioning means is removably attachable to said belt assembly.

47. A belt assembly as claimed in claim 34, wherein said positioning means are selected from a set of two or more different positioning means which are interchangeable with one another on said belt assembly.

48. A belt assembly as claimed in claim 34, wherein said elongate body includes an elongate opening therein, and wherein said positioning means comprises a plurality of post members disposed across said opening.

49. A belt assembly as claimed in claim 48, wherein said post members form a ladder-like arrangement.

50. A belt assembly as claimed in claim 48, wherein said central portion is provided with a hollow area to allow inflation of said central portion.

51. A belt assembly as claimed in claim 48, wherein said elongate body is formed from a flexible material capable of substantially conforming to the contour of the bodily surface of the patient.

52. A belt assembly as claimed in claim 34, further comprising auxiliary fastening means for removably retaining cord-like objects used during surgery.

53. A method of positioning a laparoscopic surgical instrument during a laparoscopic surgical procedure in which a laparoscopic opening is formed in a patient, comprising the steps of:
 (a) securing a belt assembly adjacent and across a bodily surface of a patient, said belt assembly comprising positioning means for providing a plurality of adjustment positions;
 (b) inserting a distal end of said laparoscopic surgical instrument into said opening;
 (c) positioning said distal end of said laparoscopic surgical instrument in a desired position engaging an internal organ, said surgical instrument including an attachment portion for adjustable attachment to said adjustment positions provided by said positioning means of said belt assembly; and
 (d) attaching said attachment portion of said surgical instrument to said positioning means of said belt assembly so that said laparoscopic surgical instrument is maintained in a desired position engaging an internal organ during the surgical procedure.

54. A method as claimed in claim 53, wherein said positioning means comprises abutment means for providing an abutment surface and said step of attaching comprises the step of placing said attachment portion of said surgical instrument into abutment with said abutment surface for retaining said attachment portion of said surgical instrument in a fixed position.

55. A method as claimed in claim 53, further comprising the step providing said positioning means as separate positioning means removably attachable to said belt assembly and attaching said separate positioning means to said belt assembly.

56. A method as claimed in claim 53, futher comprising the step providing said positioning means as interchangeable positioning means which are interchangeable on said belt assembly with other said positioning means, and interchanging one said positioning means with another said positioning means.

57. A method as claimed in claim 53, wherein said surgical instrument comprises a retractor.

58. A method as claimed in claim 57, wherein said belt assembly is secured about the abdomen of the patient.

59. A method as claimed in claim 57, wherein said belt assembly comprises a plurality of post members forming a ladder-like arrangement and said attachment means comprises an instrument hook, and said step of attaching includes locking said instrument hook around at least one of said post members.

60. A method as claimed in claim 59, wherein said belt assembly includes a central portion having a hollow area therein to allow inflation of said central portion, and said method further comprises the step of inflating said central portion so that said belt assembly fits securely across the bodily surface of the patient.

61. A method as claimed in claim 53, further comprising the step of providing a trocar port at the location of the laparoscopic opening and said step of inserting comprises inserting said distal end of said surgical instrument into the patient through said trocar port.

62. A method a claimed in claim 53, wherein said attachment means comprises an removably attachable instrument hook, and said method further comprises the step of attaching said instrument hook to said surgical instrument.

63. A method of retracting an internal organ during a laparoscopic surgical procedure in which a laparoscopic opening is formed in a patient, comprising the steps of:

(a) securing a belt assembly adjacent and across the abdomen of a patient and to an operating table beneath the patient, said belt assembly having positioning means for providing a plurality of adjustment positions;

(b) inserting a retractor into the body of the patient through said opening therein, said retractor comprising attachment means for attachment to said adjustment positions provided by said positioning means of said belt assembly;

(c) pivoting said retractor about said opening to move said retractor so as to retract said organ to a desired position; and (d) attaching said attachment means of said retractor to said positioning means of said belt assembly so that said retractor is maintained in a desired position retracting said internal organ during the surgical procedure.

64. A method as claimed in claim 63, further comprising the step of providing a trocar port at the location of the laparoscopic opening and wherein said step of inserting comprises inserting said retractor into the body of a patient through said trocar port and said step of pivoting comprises pivoting said retractor about said trocar port.

65. A method of positioning a retractor during a laproscopic surgical procedure comprising the steps of:

(a) securing a belt assembly adjacent and across a bodily surface of a patient, said belt assembly comprising positioning means for providing a plurality of adjustment positions, said positioning means comprising a plurality of post members forming a ladder-like arrangement;

(b) providing a retractor having a hook for engagement with said post members of said belt assembly; and (c) hooking said hook of said retractor to at least one of said post members to position said retractor in a desired position for the laproscopic surgical procedure.

66. A method as claimed in claim 65, wherein said hook is integrally formed with said retractor.

67. A method as claimed in claim 65, wherein said hook is removably attachable to said retractor, and said method further comprises the step of attaching said hook to said retractor.

* * * * *

UNITED STATES PATENT AND TRADEMARK OFFICE
CERTIFICATE OF CORRECTION

PATENT NO. : 5,728,047
DATED : March 17, 1998
INVENTOR(S) : Edoga

It is certified that error appears in the above-indentified patent and that said Letters Patent is hereby corrected as shown below:

Column 2, line 56, "ease" should read --case--.
Column 12, line 13, "ting" should read --ring--.

Signed and Sealed this

FourthDay of August, 1998

Attest:

BRUCE LEHMAN

Attesting Officer      Commissioner of Patents and Trademarks